(12) United States Patent
Lowe (10) Patent No.: US 7,323,003 B2
(45) Date of Patent: Jan. 29, 2008

(54) CENTERING INTRAVASCULAR FILTERS AND DEVICES AND METHODS FOR DEPLOYING AND RETRIEVING INTRAVASCULAR FILTERS

(75) Inventor: Brian J. Lowe, Zimmerman, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 747 days.

(21) Appl. No.: 10/779,152

(22) Filed: Feb. 13, 2004

(65) Prior Publication Data
US 2005/0182439 A1    Aug. 18, 2005

(51) Int. Cl.
*A61M 29/00* (2006.01)
(52) U.S. Cl. .................................. 606/200
(58) Field of Classification Search .............. 606/112, 606/113, 127, 200, 159
See application file for complete search history.

(56) References Cited

U.S. PATENT DOCUMENTS

| | | |
|---|---|---|
| 4,643,184 A | 2/1987 | Mobin-Uddin et al. |
| 5,234,458 A | 8/1993 | Metais |
| 5,242,462 A | 9/1993 | El-Nounou et al. |
| 5,344,427 A | 9/1994 | Cotenceau et al. |
| 5,350,398 A | 9/1994 | Pavenik et al. |
| 5,373,612 A | 12/1994 | Kopetzky |
| 5,383,887 A | 1/1995 | Nadal |
| 5,626,605 A | 5/1997 | Irie et al. |
| 5,634,942 A | 6/1997 | Chevillon et al. |
| 5,669,993 A | 9/1997 | Simon et al. |
| 5,746,767 A | 5/1998 | Smith |
| 5,755,790 A | 5/1998 | Chevillon et al. |
| 5,836,968 A | 11/1998 | Simon et al. |
| 5,853,420 A | 12/1998 | Chevillon et al. |
| 5,855,381 A | 1/1999 | Kirk |
| 5,938,683 A | 8/1999 | Lefebvre |
| 5,984,947 A | 11/1999 | Smith |
| 6,007,558 A | 12/1999 | Ravenscroft et al. |
| 6,013,093 A | 1/2000 | Nott et al. |
| 6,059,825 A | 5/2000 | Hobbs et al. |
| 6,156,055 A * | 12/2000 | Ravenscroft ............... 606/127 |
| 6,193,739 B1 | 2/2001 | Chevillon et al. |
| 6,214,025 B1 | 4/2001 | Thistle et al. |
| 6,231,589 B1 | 5/2001 | Wessman et al. |
| 6,258,026 B1 | 7/2001 | Ravenscroft et al. |
| 6,361,546 B1 * | 3/2002 | Khosravi .................... 606/200 |

(Continued)

FOREIGN PATENT DOCUMENTS

| | | |
|---|---|---|
| FR | 2 587 901 A | 4/1987 |
| FR | 2 672 487 A | 8/1992 |
| WO | WO 99/44542 | 9/1999 |
| WO | WO 01/82830 A2 | 11/2001 |

*Primary Examiner*—Kevin T. Truong
(74) *Attorney, Agent, or Firm*—Crompton, Seager & Tufte LLC (57) ABSTRACT

An intravascular expandable filter which has centering members that work to center the filter in a body vessel, the centering member creating a zone at the radial extent of the filter substantially parallel to the longitudinal axis of the filter. A device to deploy the filter consisting of an inner sheath with radially expandable distal arms having slots in them to receive the elongate members of the filter. A device to receive the filter consisting of a member to push a central portion of the filter into a receiving portion of the device.

6 Claims, 9 Drawing Sheets

U.S. PATENT DOCUMENTS 6,416,530 B2  7/2002  DeVries et al.
6,468,290 B1  10/2002 Weldon et al.
6,517,559 B1  2/2003  O'Connell
2005/0027314 A1  2/2005  WasDyke

* cited by examiner

CENTERING INTRAVASCULAR FILTERS AND DEVICES AND METHODS FOR DEPLOYING AND RETRIEVING INTRAVASCULAR FILTERS

FIELD

This invention relates to intravascular filters for use in a body vessel lumen and devices and methods for retrieving intravascular filters.

BACKGROUND

Intravascular filters are used to capture and retain blood clots and other emboli. The emboli may be lysed while retained by the filter or it may be retrieved, usually with the filter. Occasionally it is desirable to use an intravascular filter for an extended period of time, perhaps two to four weeks, and then retrieve it. When an intravascular filter is deployed, it is desirable to properly center the filter for maximum effectiveness and to minimize deleterious effects. Many previous filter deployment techniques consist essentially of inserting a catheter into the vasculature to the desired location and then pushing the filter from the end of the catheter. It is sometimes difficult to position the filter in the center to adjust the filter once it is in position. These devices and techniques provide minimal opportunities for adjusting the filter during or after deployment.

SUMMARY

One embodiment of the invention pertains to intravascular filters which are easier to properly center in the body vessel lumen. One example filter includes elongate members which extend radially out from a central member in a first direction. At the end of the elongate members are centering members that extend substantially parallel to the vessel walls and to the central longitudinal axis of the filter. The centering members may extends from the elongate members in a second direction opposition the first direction, the first direction, or both directions. Anchoring members may be positioned on one or more ends of the centering members. One example embodiment includes a bulge between the elongate members and the parallel portions of the centering members that may extend radially beyond the parallel portions.

Another example embodiment provides centering members which extend radially from the central filter member and may extend in the first direction. The centering members may be shorter than the elongate members and may extend radially outwardly more sharply than the elongate members. The centering members may also be substantially parallel to the elongate members and joined to the central member at a position spaced apart from the position that the central members joined at. The centering members may include atraumatic ends such as spheres or may include anchoring members such as barbs.

Another embodiment of the invention pertains to a device for deploying an intravascular filter. The device may include a first sheath having a central lumen and slots disposed around the central lumen for positioning and retaining the elongate members of the filter. The device may include a guidewire or other means for pushing the filter from the sheath. The device may also include a second sheath disposed around the first sheath, the first sheath having a radially expandable plurality of arms at the distal end. Each arm may have a slot therein for the retention and guidance of a filter. The filter may be installed by extending the first sheath distally from the second sheath so that the arms expand and thereby guide the elongate members of the filter to the desired locations.

Another embodiment of the invention pertains to a device for withdrawing an installed filter from a body vessel lumen. The device may include a capturing member which has a cylindrical lumen and an elongate member for pushing the central portion of the filter into the capturing member. One example embodiment includes a capturing member on an elongate rod and a substantially straight pushing member. The capturing member may be introduced from the upstream side of an installed intravascular filter and maneuvered through the filter so that an open end of the capturing member lumen is positioned proximate the central portion of the filter. The pushing member may then be used to push the filter into the capturing member. As the filter is pushed into the capturing member, the radially expanded elongate members of the filter are compressed. The filter may then be removed or moved into a catheter and then removed. Another example embodiment includes a pushing member which has a distal end that may be substantially parallel to the body of the pushing member and facing proximally. It has a configuration similar to a hook. This example embodiment may be best suited for withdrawing the filter from downstream. The pushing member is maneuvered so that the distal end is able to push on the central member of the filter. The capturing member is maneuvered to the opposite side of the central filter member. The pushing member can then be withdrawn to urge the filter into the capturing member. Alternatively, the pushing member can be held in place to prevent the filter from moving and the capturing member can be drawn over the filter.

The above summary of some embodiments is not intended to describe each disclosed embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings in which.

DETAILED DESCRIPTION OF SELECTED EMBODIMENTS

The following detailed description should be read with reference to the drawings, in which like elements in different drawings are numbered identically. The drawings which are not necessarily to scale, depict selected embodiments and are not intended to limit the scope of the invention.

Figure 1:
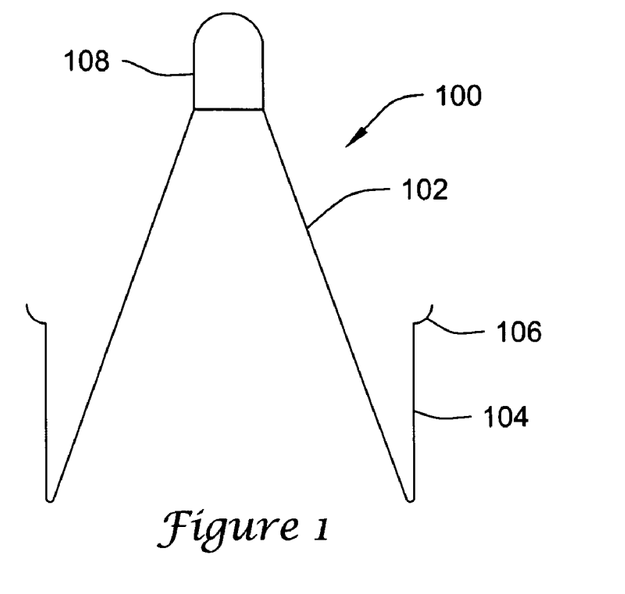
FIG. 1 is a diagrammatic side view of an intravascular filter embodiment.

FIG. 1 is a diagrammatic side view of an intravascular filter 100. Filter 100 includes elongate members 102, centering members 104 disposed at the ends of elongate members 102, and may include anchoring members 106 disposed on the centering members. Elongate members 102 radially extend from central member 108. Filter 100 may include six, eight, or other suitable number of elongate member 102, which are substantially evenly disposed about the filter. Centering members 104 are generally parallel to the longitudinal axis of the filter and may optionally include anchor members 106. Anchor members 106 may be barbs or other suitable device for retain the filter in place in the body vessel. Elongate members 102 and Centering members 104 may be made from stainless steel, nickel-titanium alloy, or other suitable material. In use, the filter may be compressed and loaded into a catheter or a deployment device as described below. The catheter is introduced into a body vessel such as the vena cava and the filter may be urged from the end of the catheter. The filter expands as it leaves the catheter. When the filter is expanded against the walls of the body vessel, centering elements 104 provide good contact against the wall of the body vessel and generally lay flat against the vessel wall. This permits the filter to properly center in the body vessel.

Figure 2:
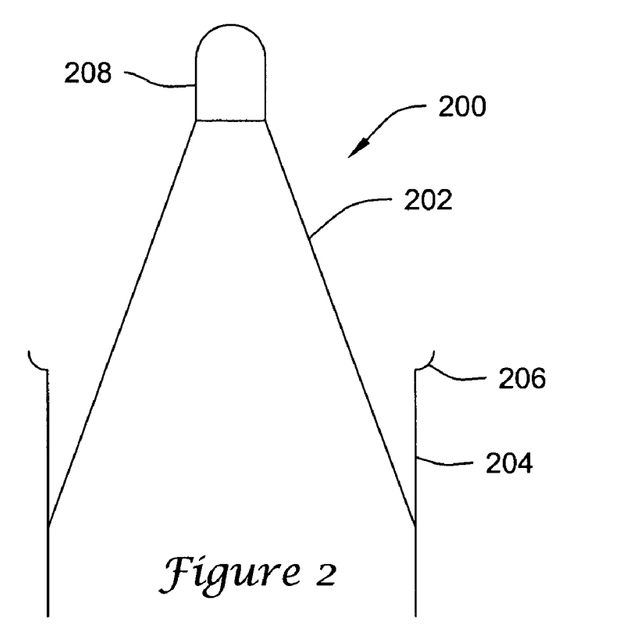
FIG. 2 is a diagrammatic side view of another intravascular filter embodiment.

FIG. 2 is a diagrammatic side view of another intravascular filter 200. Filter 200 is similar to filter 100 and includes elongate members 202, centering members 204 and may include anchoring members 206. In this configuration, centering members 206 extend in both directions from the attachment point. Centering members 206 may be longer than centering members 106 or may be substantially the same length.

Figure 3:
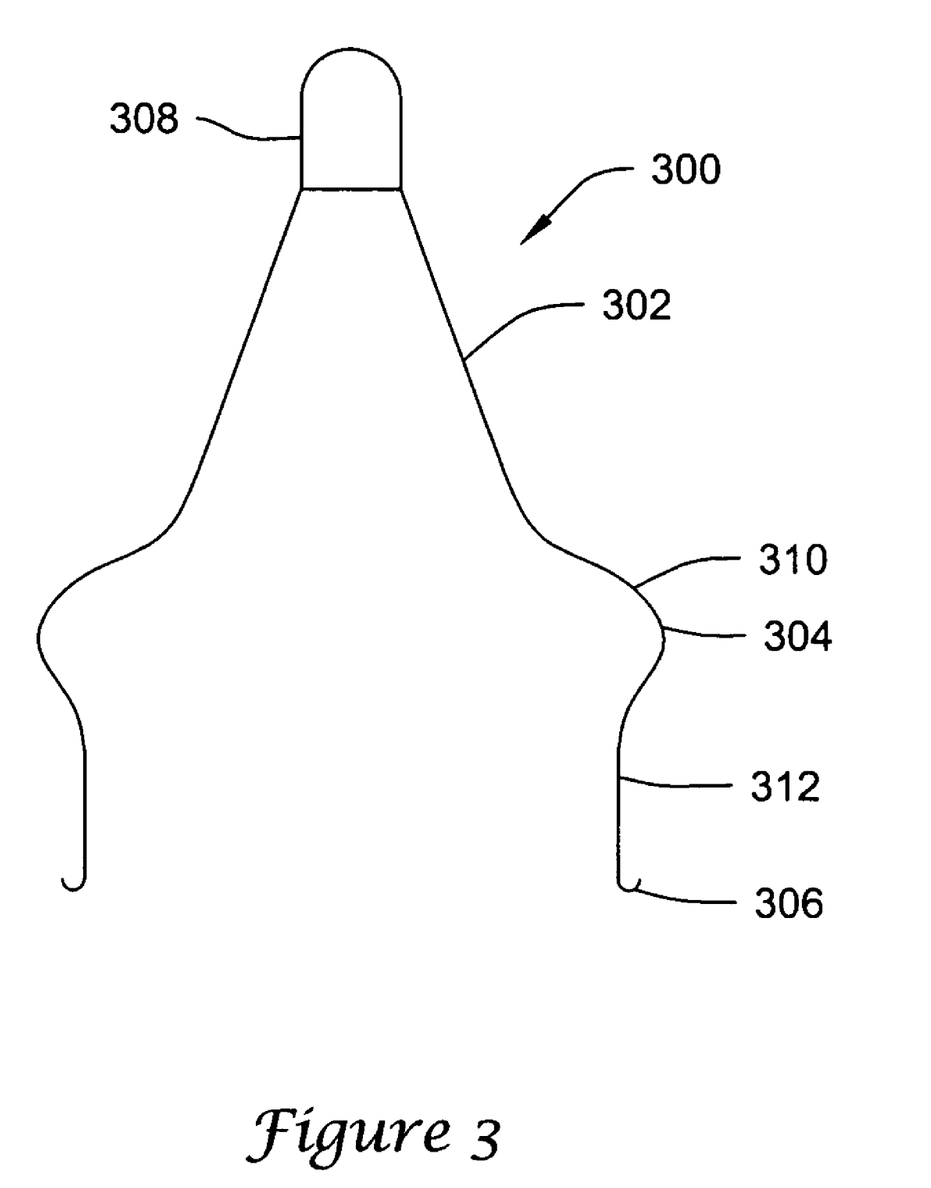
FIG. 3 is a diagrammatic side view of another intravascular filter embodiment.

FIG. 3 is a diagrammatic side view of another intravascular filter 300. Filter 300 includes elongate members 302 connected to central member 308. Centering members 304 are attached to the end of elongate members 302 and extend in generally the same direction as the elongate members. Centering members 304 include bulge portion 310 and straight portion 312. Anchoring members 306 may be attached to the centering members. Bulge portion 310 may extend radially outwards beyond straight portion 312. If the filter is deployed central member 308 first, bulge portion 310 may help to center the filter before anchoring member 306 contact the vessel wall, while straight portion may serve to further straighten the filter. The curves may also reduce any trauma to the vessel wall.

Figure 4:
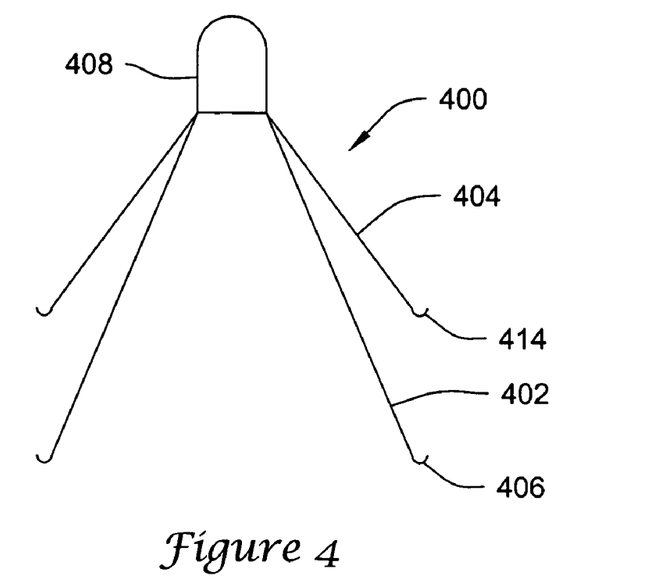
FIG. 4 is a diagrammatic side view of another intravascular filter embodiment.

FIG. 4 is a diagrammatic side view of another intravascular filter 400. Filter 400 includes elongate members 402 extending from central member 408, which may have anchoring members 406 disposed on the ends. Centering members 404 also extend radially from central member 408. Centering members 404 may include anchoring members 406 or atraumatic members 414 disposed on the ends. Atraumatic ends may be plates or spheres or other suitable configuration. Centering members 404 generally extend radially from the central member more sharply than elongate members 402. In one embodiment, centering members may extend essentially straight out, with little or no longitudinal extension. When expanded, the free ends of centering members 404 and elongate members 402 are substantially the same distance from a central axis of the filter. Therefore, when expanded, the centering members in combination with the elongate members help to center the filter.

Figure 5:
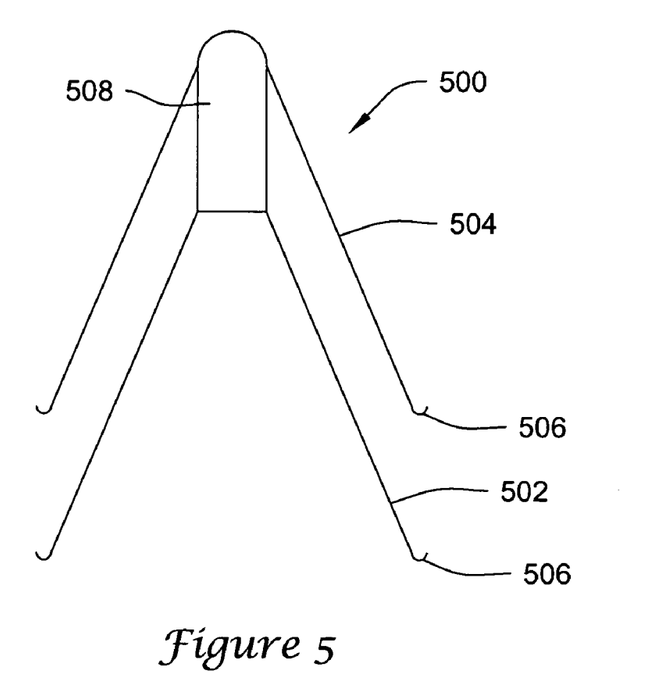
FIG. 5 is a diagrammatic side view of another intravascular filter embodiment.

FIG. 5 is a diagrammatic side view of another intravascular filter 500. Filter 500 includes elongate members 502 attached to central member 508. Anchoring members 506 may be disposed on the ends of elongate member 502. Attached to central member 508 at a distance from the attachment point of the elongate members are centering members 504. Centering members 504 may be substantially parallel to elongate members 502 or may be configured like the centering members of the embodiment of FIG. 4. Centering members may include anchoring members 506 or may include atraumatic ends.

Figure 6:
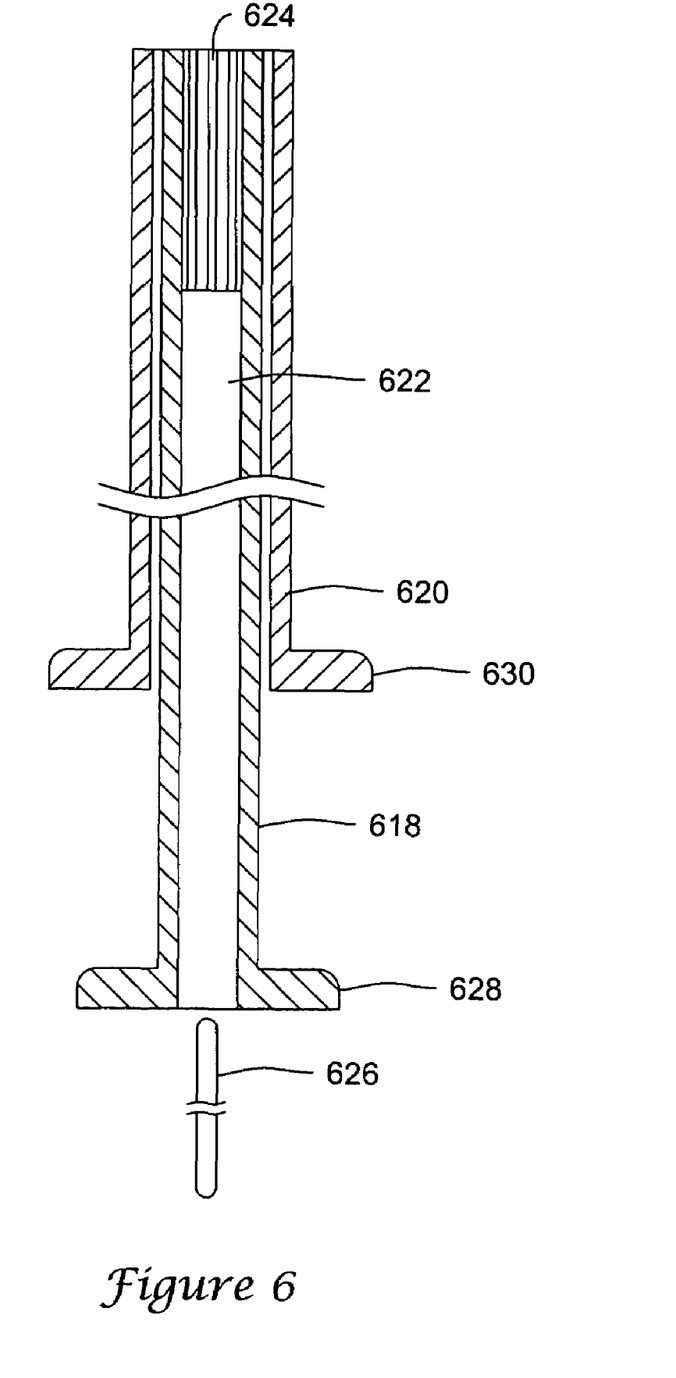
FIG. 6 is a cross-sectional side view of a filter deployment device.

FIG. 6 is a cross-sectional side view of a filter deployment device 616. Device 616 includes a first sheath slidably 618 disposed in a second sheath 620. First sheath has a lumen 622 which is sized to contain a filter in a compressed state. Slots 624 are located at a distal end of the sheath and may serve to position the elongate members of a filter and retain them in position prior to and during deployment. Device 616 may also include a guidewire or other suitable wire 626, which may be used to urge the filter from the deployment device. Sheath 618 may include stop 628 and sheath 620 may include stop 630.

Figure 7:
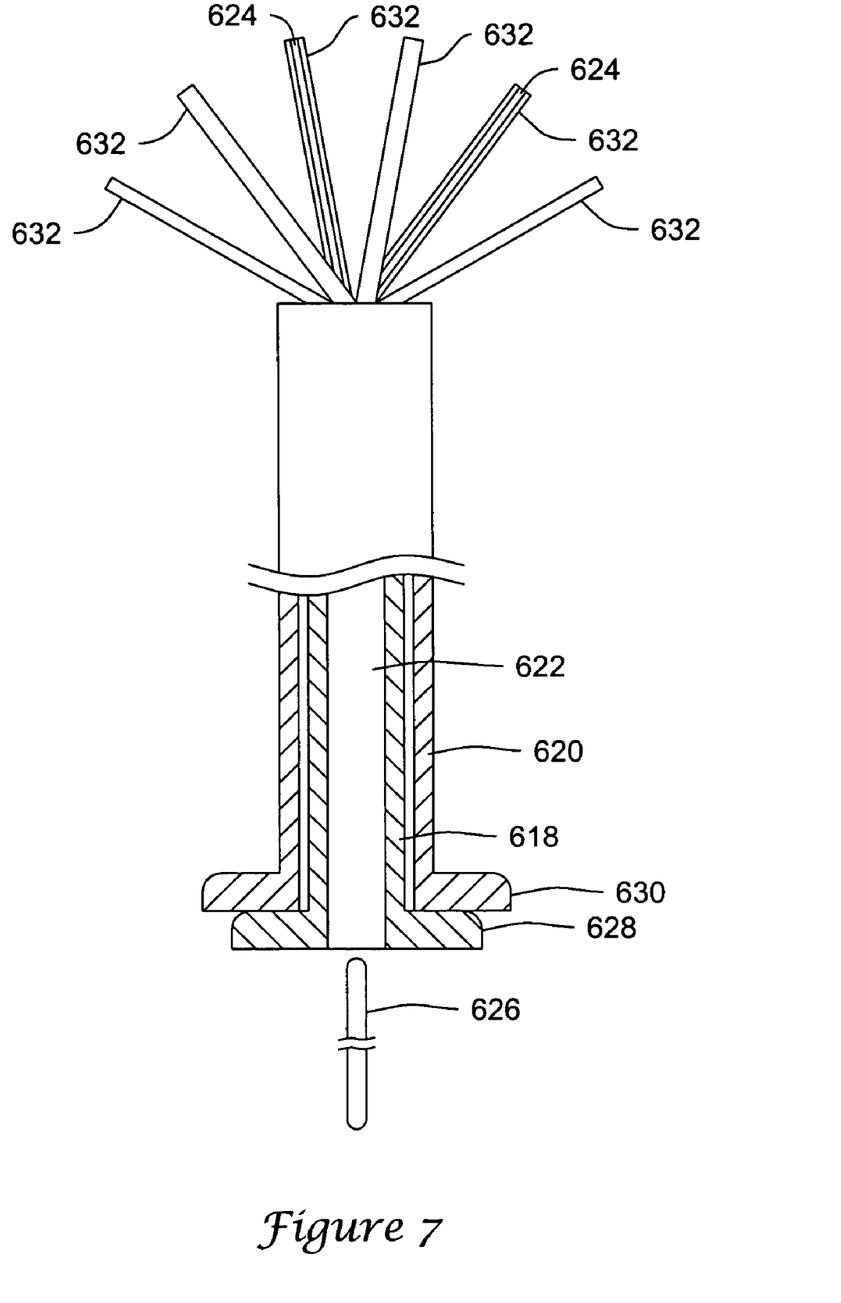
FIG. 7 is a partial cross-sectional side view of the filter deployment device of FIG. 6.

As can be seen in FIG. 7, which is a partial cross-sectional side view of the filter deployment device 600, when stop 628 is proximate stop 630, the distal end of sheath 618 is distal the distal end of sheath 620. This permits arms 632 to expand and deploy the filter in the desired filter. Wire 626 may be used to urge the filter from the device, if desired. Because the elongate members of the filter are retains in slots 624, filter deployment device 600 may be used to accurately position a filter.

Figure 8:
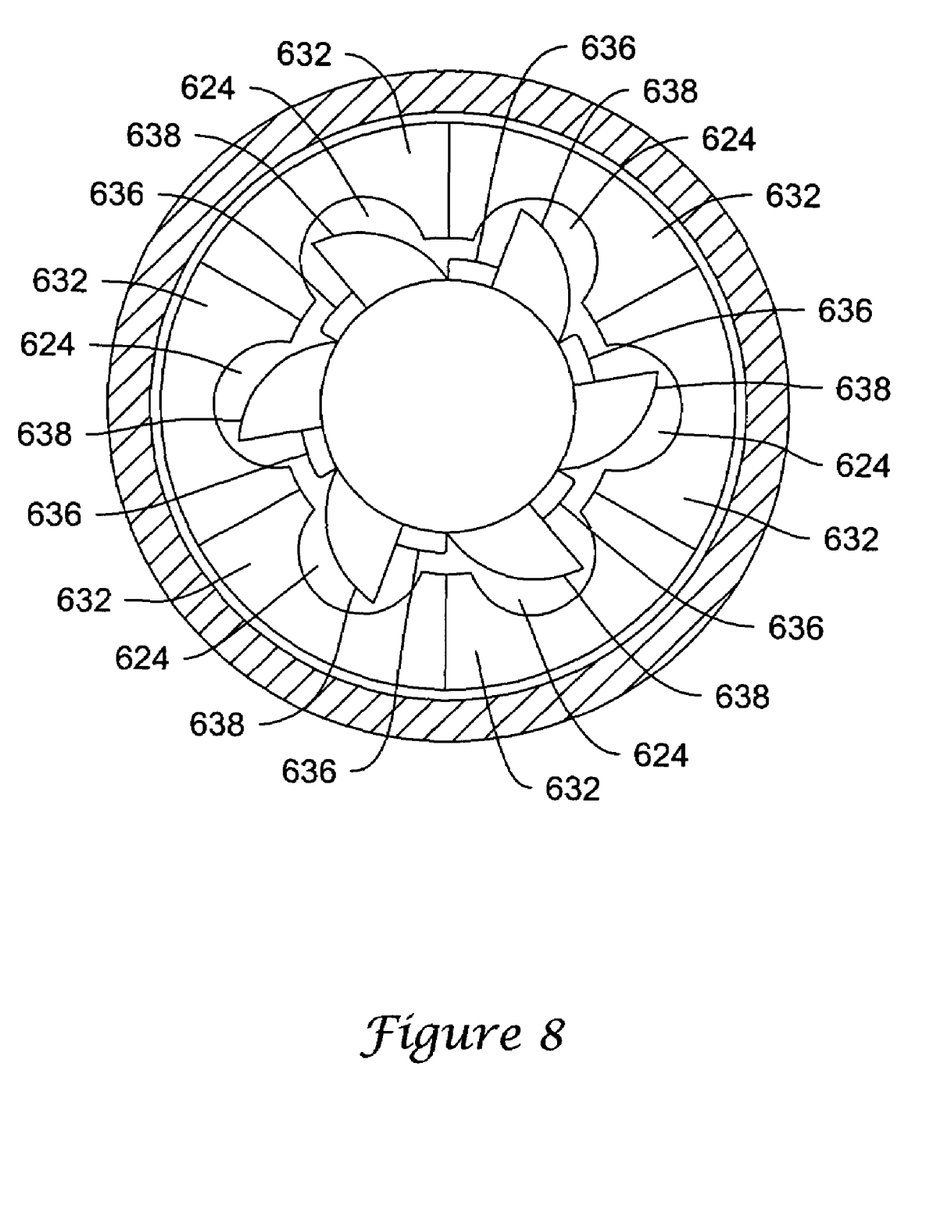
FIG. 8 is an end view of the filter deployment device of FIG. 6 with an example filter loaded therein.

FIG. 8 is an end view of filter deployment device 616 with an example filter 634 loaded therein. Filter 634 may be a Greenfield type filter with radially expanding elongate filter elements 636 including anchoring elements 638. Elongate filter elements 636 are biased to expand outward. Sheath 618 has expandable arms 632 with slots 624 formed therein. Sheath 618 is disposed within sheath 620 and arms 632 are constrained by sheath 620. Filter 634 is loaded in sheath 618 such that each elongate filter element 636 is loaded into a slot 624. Because filter elements 636 are biased to expand outward, they will generally stay within slots 624 until moved out of them. Thus if sheath 618 is moved distally out of sheath 620 so that arms 632 expand, elongate filter elements 636 will expand with the arms.

Figure 9A:
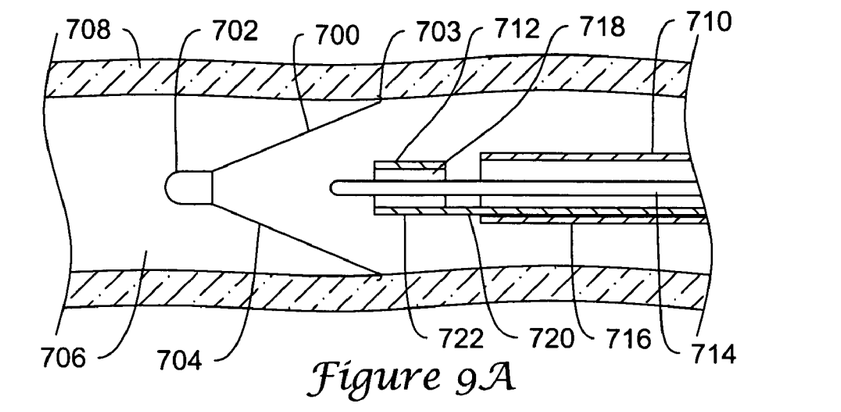
FIG. 9*a* is a diagrammatic side view of a filter retrieval device, filter and body vessel.

FIG. 9a is a diagrammatic side view of a filter retrieval device, filter and body vessel. Filter 700 includes central portion 702 and elongate filter members 704 that are biased to an expanded position, and may include anchor members 703. Filter 700 is installed in a lumen 706 of a body vessel 708. Filter retrieval device 710 is urged into the body vessel lumen to retrieve the filter. Filter retrieval device 710 includes a capturing member 712, an elongate member 714 and may include a sheath 716. Capturing member 712 has a capturing portion 722 having a lumen 718 with proximal and distal openings. Capturing portion 722 is disposed on a wire 720 which does not occlude the proximal or distal openings and may be slidably disposed within the catheter. Capturing portion lumen 718 is large enough to receive filter 700 yet small enough to hold elongate filter members in a constrained position. Elongate member 714 may be a wire, rod or suitable instrument that should have sufficient compressive strength to push on filter 700. Catheter 716 may be large enough to receive capturing member 712, or alternatively, may be large enough to abut capturing portion 722.

Figure 9B:
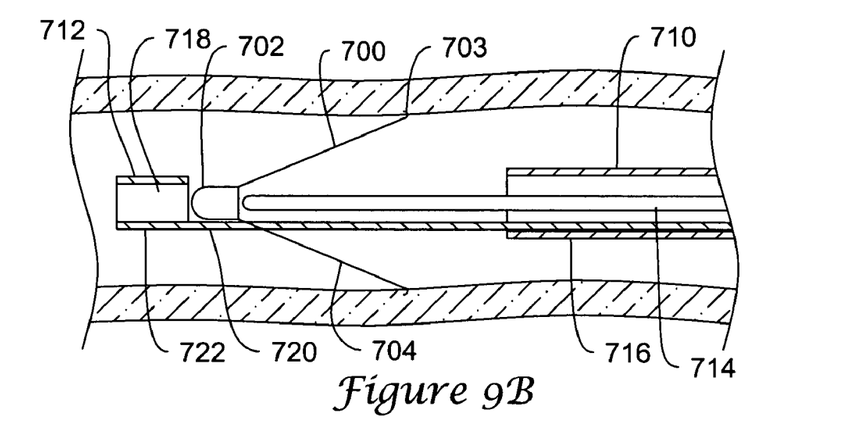
FIG. 9*b* is a diagrammatic side view of the filter retrieval device of FIG. 9*a* operating on a filter in a body vessel.
Figure 9C:
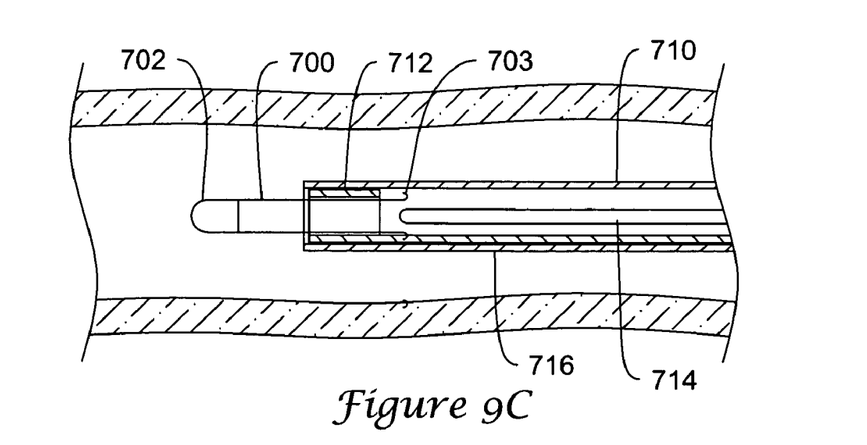
FIG. 9*c* is a diagrammatic side view of the filter retrieval device of FIG. 9*a* operating on a filter in a body vessel.

As can be seen in FIG. 9b, to retrieve filter 700, capturing member 712 is positioned proximate and distal central portion 702 of filter 700. (All use of the terms "proximal" and "distal" are with reference to the device and not with reference to the filter or the vasculature.) Elongate member 714 may be positioned to be proximate and proximal central portion 702. Capturing member 712 may be moved proximally to receive central portion 702 and elongate filter members 704 of filter 700. As elongate filter members 702 are received in capturing portion 722, they are moved radially inward to a compressed position. When capturing portion 722 reaches the other end of filter 704, the filter may be in a retracted state and in suitable condition to retrieve. Lumen 718 extends for some distance longitudinally. When retrieving a filter, this longitudinal distance may keep the filter in a generally longitudinal position parallel to filter retrieval device 710. One example benefit is that control over the filter and the filter position is enhanced. Capturing member 712 and elongate member 714 may then be moved proximally out of body vessel 708 along with filter 700, which is retained. Alternatively, capturing member 712 and elongate member 714 may be moved into catheter 716, and then filter retrieval device 710 may be moved out of body vessel 708. Part of this process is depicted in FIG. 9c, which is a diagrammatic side view of the filter retrieval device 710 operating on filter 700 in body vessel 708.

Figure 10A:
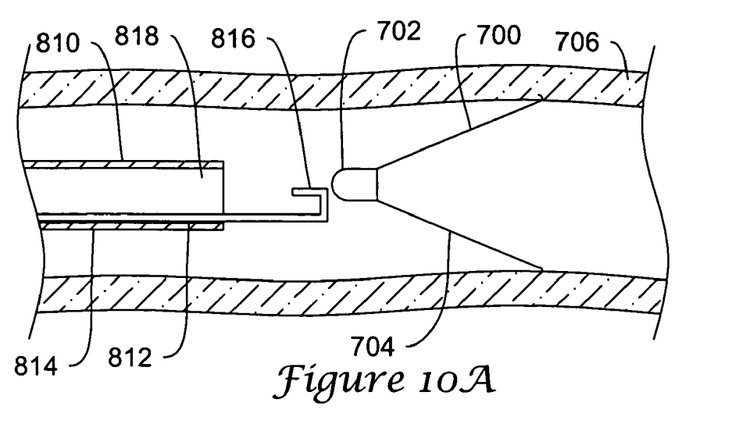
FIG. 10a is a diagrammatic side view of another filter retrieval device, filter and body vessel.
Figure 10B:
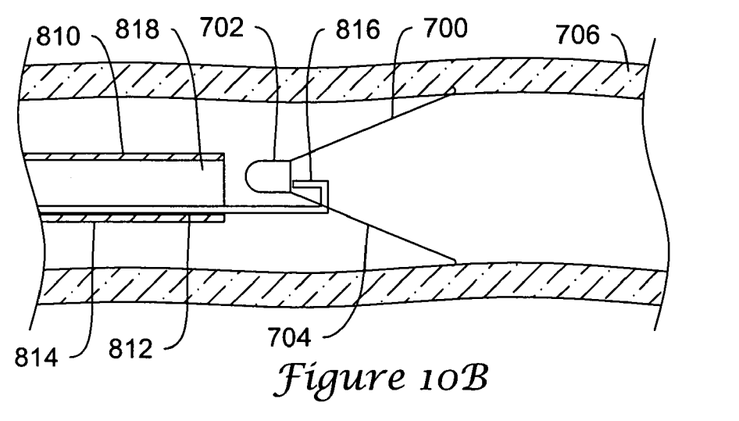
FIG. 10b is a diagrammatic side view of the filter retrieval device of FIG. 10a operating on a filter in a body vessel.
Figure 10C:
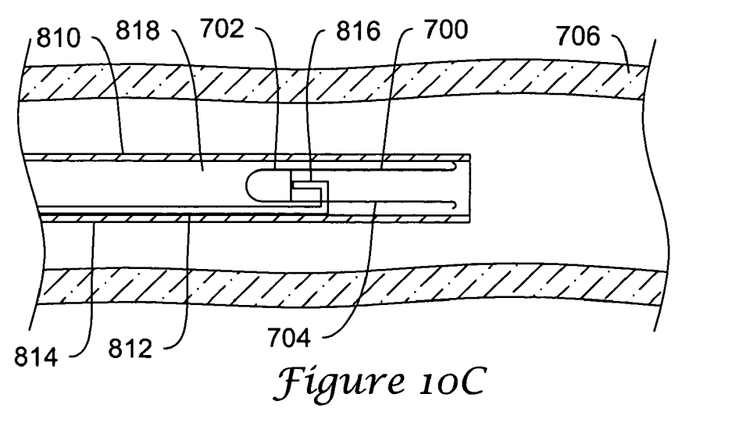
FIG. 10c is a diagrammatic side view of the filter retrieval device of FIG. 10a operating on a filter in a body vessel.

FIG. 10a is a diagrammatic side view of another filter retrieval device, filter and body vessel. Filter 700 is disposed in a body vessel lumen 706. Filter retrieval device 810 includes capturing member 814 and elongate member 812. Elongate member 812 is generally hook-shaped with a distal end configured to be able to push central portion of filter towards capturing member 814. Elongate member 812 therefore has a distal portion 816 which extends back proximally. The distal-most portion of elongate member 812 may be rounded or wedge shaped to ease passage distally through elongate filter members 704, and may also be blunt to prevent trauma to the body vessel wall. Capturing member 814 has a lumen 818 which has a distal opening and is deep enough to receive filter 700. Capturing member 814 may be a catheter, for example. To retrieve filter 700, distal portion 816 of elongate member 812 is moved to be distal and proximate central member 702 of filter 700. Capturing member 814 is moved to be proximate central member 702, as can be seen in FIG. 10b, which is a diagrammatic side view of filter retrieval device 810 operating on filter 700 in body vessel 706. While holding elongate member 812 in place, capturing member can then be moved distally to contract and receive filter 700, in a manner similar to that describe above. When the filter is in lumen 818, as can be seen in FIG. 10c, retrieval device 810 may then be removed from the body vessel, with the filter inside.

Figure 11:
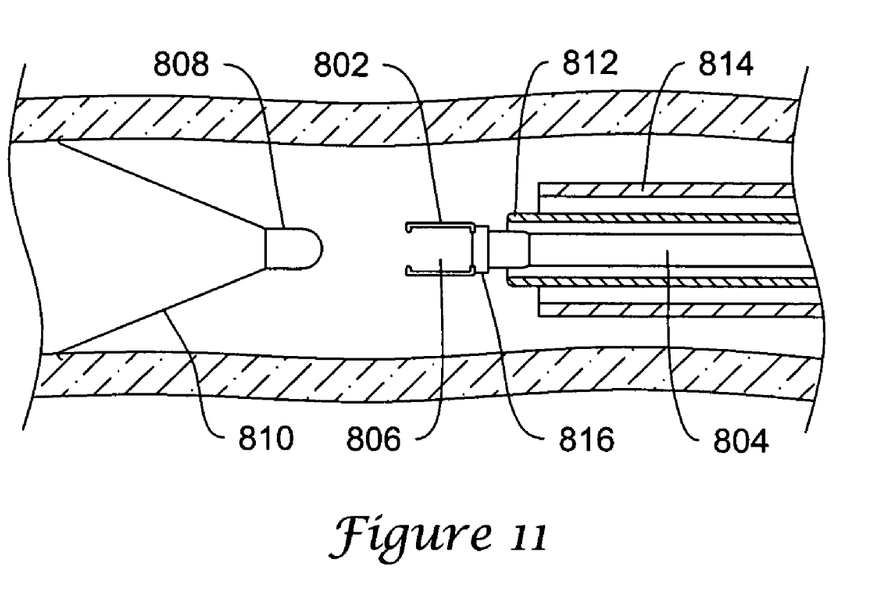
FIG. 11 is a cross-sectional side view of another filter retrieval device.

FIG. 11 is a cross-sectional side view of the distal portion of another filter retrieval device disposed in a body lumen proximal a filter 810. Filter retrieval device 800 includes retrieval prongs 802 attached to a guidewire 804. Retrieval prongs 802 may be attached by a collet 804 or by other suitable means. Filter retrieval device 800 may include 3, 4, 5 or other suitable number of retrieval prongs. The retrieval prongs are arranged around a central receiving cavity 806, which is configured to receive a central portion 808 of a filter 810. In one configuration, collet 804 is relatively flexible such that when filter retrieval device 800 is advanced over central portion 808 of filter 810, the prongs open to receive the central portion and return to an unexpanded position once the central portion is in central receiving cavity 806. Retrieval prongs 804 have a distal lip to retain the central portion of a filter once the filter is in the cavity. In another configuration, retrieval prongs 802 are somewhat flexible and bend outwards as the filter retrieval device is slid over central portion 808 and return to their original position once the central portion is in central receiving cavity 806. Once the central portion is in central receiving cavity 806, a catheter 812 may be advanced over retrieval prongs 802 to retain them in position. Catheter 812, with central portion 808 of filter 810 secured within, may then be withdrawn in catheter 814. Retrieval prongs 802 may be made from any suitable biocompatible material such as stainless steel, nitinol, nylon, or other suitable material. They may include gold or platinum markings for increased radiopacity. Collet 804 may be made from a biocompatible polymer of suitable flexibility and strength or may be made from metal. Guidewire 804 may be made like any suitable intravascular guidewire. Catheter 812 may be made from hypotubing or other suitable material. Catheter 814 may be any suitable guide or retrieval catheter.

Numerous advantages of the invention covered by this document have been set forth in the foregoing description. It will be understood, however, that this disclosure is, in many respects, only illustrative. Changes may be made in details, particularly in matters of shape, size, and arrangement of parts or order of steps without exceeding the scope of the invention. The invention's scope is, of course, defined in the language in which the appended claims are expressed.

The invention claimed is:

1. A deployment device for an expandable filter, the expandable filter having a plurality of elongate elements, the deployment device comprising:
   a first sheath having a central lumen extending from a first end to a second end;
   a plurality of arms extending from the first sheath; and
   a plurality of slots, each of the plurality of slots disposed within one of the plurality of arms for positioning the plurality of elongate elements;
   wherein the plurality of elongate elements fit into the plurality of slots.

2. The device of claim 1, wherein the plurality of elongate elements and the plurality of slots are equal in number.

3. The device of claim 1, further comprising a second sheath slidably disposed over the first sheath.

4. The device of claim 3, wherein each of the plurality of arms have a first free end and a second joined end.

5. The device of claim 3, wherein the first sheath comprises a first stop and the second sheath comprises a second stop, wherein when the first stop is against the second stop, the arms are expanded.

6. The device of claim 1, wherein the arms are in an expanded position when unconstrained.

* * * * *